United States Patent [19]
Faries, Jr. et al.

[11] Patent Number: 5,522,095
[45] Date of Patent: *Jun. 4, 1996

[54] METHOD AND APPARATUS FOR PRODUCING STERILE SURGICAL MEDIA

[75] Inventors: Durward I. Faries, Jr., McLean, Va.; Bruce R. Heymann, Silver Spring, Md.

[73] Assignee: O.R. Solutions, Inc., Chantilly, Va.

[*] Notice: The term of this patent shall not extend beyond the expiration date of Pat. No. 5,333,326.

[21] Appl. No.: 399,975

[22] Filed: Mar. 6, 1995

Related U.S. Application Data

[60] Continuation-in-part of Ser. No. 224,378, Apr. 7, 1994, Pat. No. 5,429,801, which is a division of Ser. No. 33,639, Mar. 16, 1993, Pat. No. 5,333,326.

[51] Int. Cl.⁶ .................................................. F25C 1/00
[52] U.S. Cl. ...................... 4/639; 62/66; 220/577
[58] Field of Search ............... 4/639; 604/113; 607/113; 62/66 X; 422/40, 41; 220/577 X

[56] References Cited

U.S. PATENT DOCUMENTS

| | | |
|---|---|---|
| 4,393,659 | 7/1983 | Keyes et al. . |
| 4,474,016 | 10/1984 | Winchell . |
| 4,782,835 | 11/1988 | Bernandini . |
| 4,934,152 | 6/1990 | Templeton . |
| 5,042,455 | 8/1991 | Yue et al. . |
| 5,163,299 | 11/1992 | Faries, Jr. et al. . |
| 5,331,820 | 7/1994 | Faries et al. . |
| 5,333,326 | 8/1994 | Faries et al. . |
| 5,429,801 | 7/1995 | Faries, Jr. et al. . |

*Primary Examiner*—John C. Fox

[57] ABSTRACT

The features of a surgical slush machine are augmented by supplemental basins for surgical liquid to thereby permit simultaneous availability of warm and/or chilled liquid and/or surgical slush. The basins are disposed in close sequential adjacency, and a common sterile drape is disposed over and contoured to all of the basins to provide separate sterile receptacles in the drape for the various sterile media. Basin centering indicia on the drape facilitate deployment of the drape relative to the basins and selectively removable covers insulate and protect the sterile medium between periods of use. Cooling and heating of the respective basins is effected independently with individual power controls.

44 Claims, 6 Drawing Sheets

METHOD AND APPARATUS FOR PRODUCING STERILE SURGICAL MEDIA

CROSS-REFERENCE TO RELATED APPLICATIONS

This application is a continuation-in-part of U.S. patent application Ser. No. 08/224,378, filed Apr. 7, 1994, now U.S. Pat. No. 5,429,801, which is a division of U.S. patent application Ser. No. 08/033,639, filed Mar. 16, 1993, now U.S. Pat. No. 5,333,326. The disclosures from that application and patent are incorporated herein in their entireties.

BACKGROUND OF THE INVENTION

1. Technical Field

The present invention pertains to improvements in methods and apparatus for producing surgical sterile fluid media. In particular, the invention is an improvement of the methods and apparatus disclosed in U.S. Pat. Nos. 4,393,659 (Keyes et al) and 4,934,152 (Templeton) and U.S. patent application Ser. No. 08/213,807 (Faries, et al). The disclosures in those patents are expressly incorporated herein in their entireties by this reference.

2. Discussion of the Prior Art

The Keyes et al patent discloses a surgical slush producing system having a cabinet with a heat transfer basin at its top surface. A refrigeration mechanism in the cabinet takes the form of a closed refrigeration loop including: an evaporator in heat exchange relation to the exterior of the heat transfer basin; a compressor; a condenser; and a refrigeration expansion control, all located within the cabinet. A separate product basin is configured to be removably received in the heat transfer basin. Spacers, in the form of short cylindrical stubs or buttons are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile sheet of material, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency in the product basin.

As noted in the Templeton patent, the above-described system has a number of disadvantages. In particular, the separate product basin must be removed and re-sterilized after each use. Additionally, the glycol or other thermal transfer medium is typically highly flammable or toxic and, in any event, complicates the procedure. The Templeton patent discloses a solution to these problems by constructing an entirely new apparatus whereby the product basin is eliminated in favor of a sterilized drape impervious to the sterile surgical liquid, the drape being made to conform to the basin and directly receive the sterile liquid. Congealed liquid is scraped off the sides of the conformed drape receptacle to form the desired slush.

In addition, Templeton also provides an electrical heater disposed at the bottom of the basin to convert the sterile slush to warmed liquid, or to heat additional sterile liquid added to the basin. Templeton describes the need for such warmed sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both the sterile warmed liquid and the sterile surgical slush, and, on occasion, a supply of near-freezing liquid-state sterile fluid. For example, if the surgical slush is not at the desired consistency (e.g., too thick), the availability of warmed sterile liquid to be added to the slush permits rapid adjustability of the slush consistency. Likewise, maintaining instruments at or near body temperature during surgery is a desirable feature permitted by warmed sterile liquid. Of course, if the warmed sterile liquid is simultaneously available with the surgical slush, there is no need to wait for the slush to melt at the end of the surgical procedure. Finally, the simultaneous and separate provision of slush and warm and near-freezing liquid permits different sterile media to be used as is sometimes necessary for various surgical procedures.

OBJECTS AND SUMMARY OF THE INVENTION

It is an object of the present invention to provide a method and apparatus for simultaneously providing separate surgical slush and/or warmed and/or cooled surgical liquid in close adjacency one to another during a surgical procedure.

It is another object of the present invention to provide a sterile drape receptacle arrangement for a unit capable of simultaneously providing sterile surgical slush and sterile heated and/or cooled liquid.

It is a yet further object of the present invention to provide thermal and pathogen insulation for sterile medium.

In accordance with the present invention separate basins of the type, for example, disclosed in the Templeton patent, for containing warmed sterile surgical liquid, near-freezing cooled sterile surgical liquid and sterile surgical slush are arranged in closely adjacent or successively adjacent proximity one to another. Each additional basin may be a separate unit secured to the pre-existing unit, or may be constructed as part of an integral cabinet for housing each of the basins. Each basin has its own power control and temperature control, preferably located on the top surface of the corresponding basin unit. If the warmed liquid needs to be rapidly cooled, slush or cooled liquid can be transferred immediately from the appropriate basin; likewise, if the slush is too thick, warmed liquid can be immediately transferred from the warming basin.

A single surgical drape covers all of the basins and contains the warmed and chilled liquid and the slush in a sterile manner. The drape, thusly serving as two or more receptacles, depending on the number of sterile fluid media required, may preferably be provided with two or more centering indicia (e.g., colored dots, or the like) positioned to correspond to the centers of the two or more basins. The drape may thus be easily positioned relative to the basins during deployment to provide the required sterile protection in the operating room. Selectively positionable covers are provided to thermally insulate the medium when immediate access is not required and to reduce the exposure of the medium to airborne pathogens.

The above and still further objects, features and advantages of the present invention will be apparent upon consideration of the following detailed description of the spe-

DESCRIPTION OF THE PREFERRED EMBODIMENTS

Figure 1:
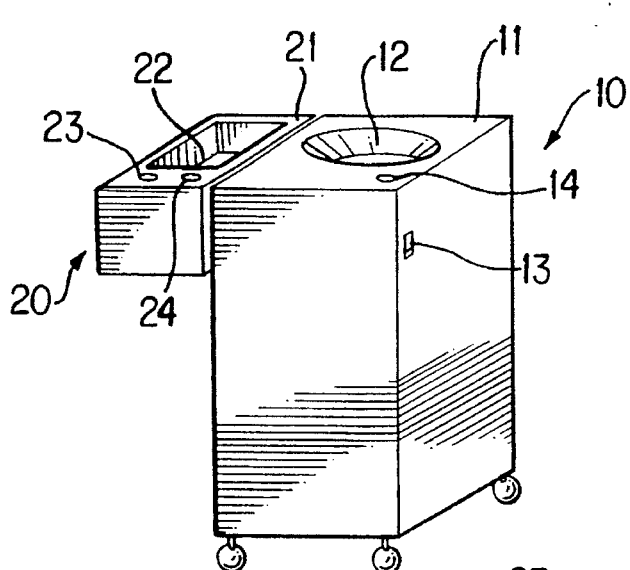
FIG. 1 is a view in perspective of a surgical slush unit and warming unit combination provided in accordance with the present invention.

Referring to FIG. 1 of the accompanying drawings, a surgical slush unit 10 has a heating unit 20 secured thereto. Surgical slush unit 10 may, for example, be configured as the type described and illustrated in the aforementioned Templeton patent, although other configurations are suitable within the scope of the present invention. Surgical slush unit 10 has a top surface 11 with a slush basin 12 recessed therein. A power switch 13 is disposed on the sidewall of the cabinet in the Templeton unit. An additional cooling unit temperature controller/indicator switch 14 is shown disposed on the unit top surface 11. In the manner described in the Templeton patent, a suitable sterile liquid, such as a saline solution, is cooled in basin 12 to form surgical slush. In use, the top surface 11 and basin 12 are covered with a sterile liquid impervious drape (not shown in FIG. 1) that can be recessed into the basin. As contemplated by Templeton, ice formed on the sides of the drape is scraped off the drape surface to form slush. In the system described in U.S. Pat. No. 5,163,299 (Faries et al), the formed ice is removed from the drape by gently lifting the drape and shaking it slightly. In either event, surgical slush at the desired consistency may be formed in the receptacle provided by the drape in the slush basin.

Heating unit 20 may be secured to a sidewall of a cooling unit cabinet such that the top surface 21 of the heating unit is a substantially coplanar extension of the slush unit top surface 11. Attachment of the heating unit 20 to the surgical slush unit cabinet may be by bolts, brackets or other suitable means. A warming basin 22 is recessed into top surface 21.

A heater power switch 23 and a temperature controller/indicator 24 are provided on top surface 21 adjacent the warming basin to maintain the temperature of the sterile medium at a temperature somewhat above normal operating room temperature.

Figure 2:
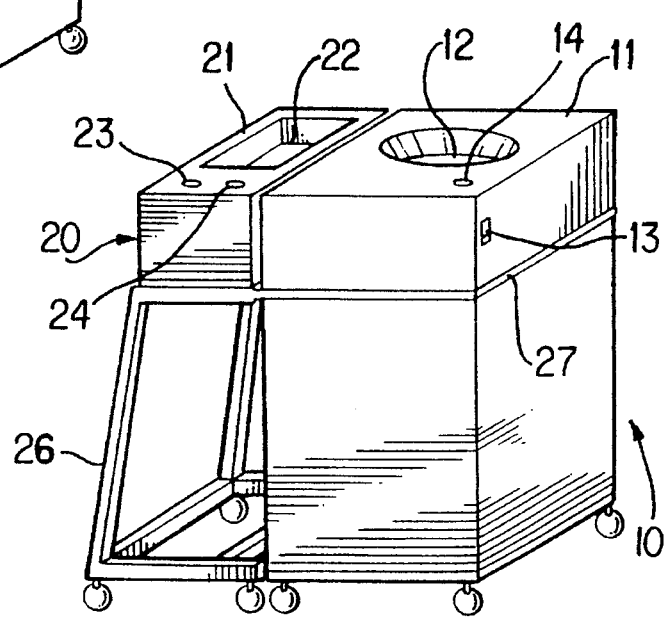
FIG. 2 is a view in perspective of a surgical slush unit and warming unit having a different means for attaching the units together.

Another technique for securing heater unit 20 to pre-existing surgical slush machine 10 is illustrated in FIG. 2. Specifically, a separate wheeled stand 26 has a horizontal support surface for heater unit 20. The thusly supported heater unit has its top surface 21 substantially coplanar with top surface 11 of the surgical slush unit. A belt or strap 27 extends from stand 26 to circumscribe the cabinet of the surgical slush unit 10, thereby preventing inadvertent separation of the slush forming and heating units.

Figure 3:
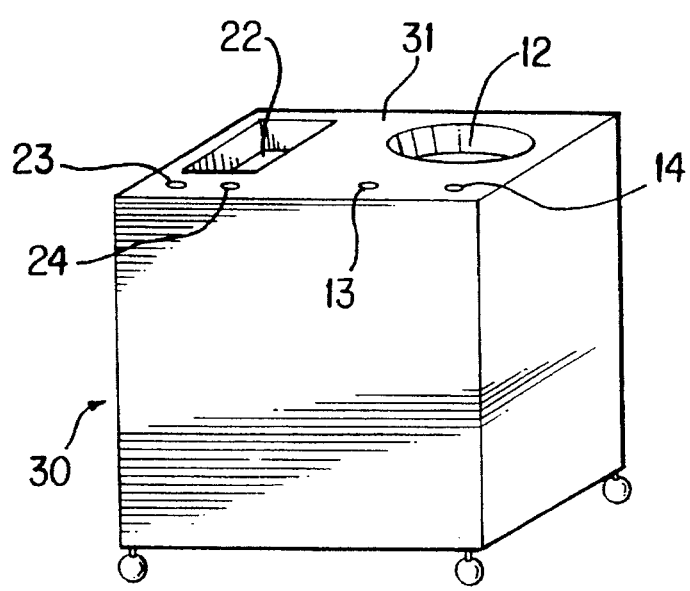
FIG. 3 is a view in perspective of a single unit containing adjacent separate heating and cooling basins pursuant to the present invention.

In FIG. 3 there is illustrated an integral assembly 30 wherein a slush basin 12 for slush phase medium and a warming basin 22 for heated liquid phase medium are recessed into the top surface 31 of a common cabinet. Also disposed on top surface 31 are a cooling unit power switch 13, a cooling unit temperature controller/indicator 14, a heater power switch 23 and a heater unit temperature controller/indicator 24

Figure 4:
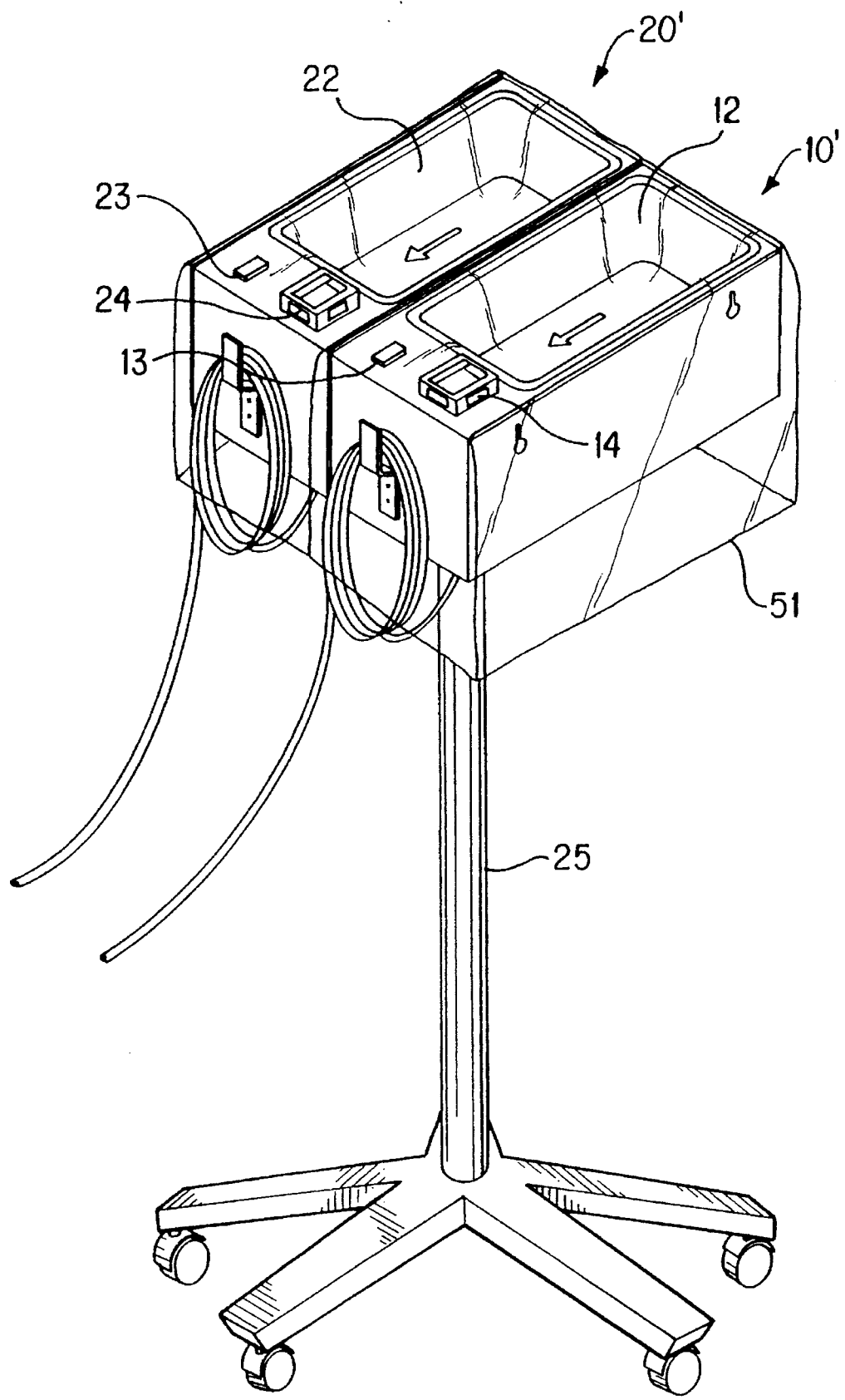
FIG. 4 is a view in perspective of a pedestal mounted double unit containing separate adjacent heating and cooling units pursuant to the present invention.
Figure 5:
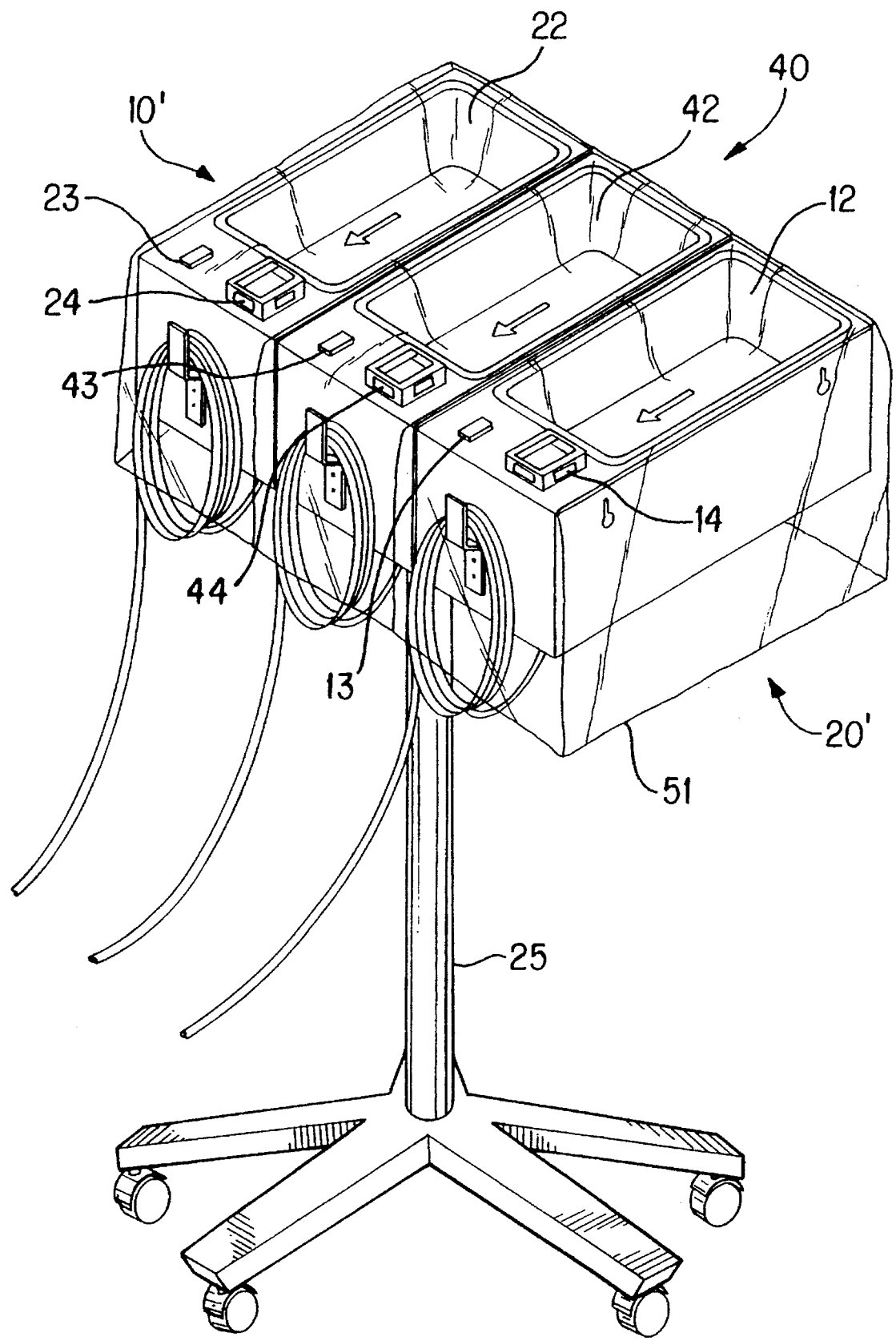
FIG. 5 is a view in perspective of a pedestal mounted triple unit containing separate successively adjacent heating, chilling and slush forming units pursuant to the present invention.

FIGS. 4 and 5 show a two and a three basin coplanar assembly, respectively, each covered by a drape. FIG. 4 illustrates a surgical slush unit 10' attached to and adjacent a heater unit 20' and jointly supported by a unitary pedestal base 25. FIG. 5 shows a near-freezing chilled liquid unit 40 mounted adjacently between the slush and heater units, 10' and 20', respectively, all supported by pedestal 25. The chiller unit 40 is provided for those procedures requiring ready access to a liquid state chilled surgical liquid and is included with a basin 42, a separate power switch 43 and controller/indicator 44. A sterile drape 51, described hereinafter, is shown overlaying the basin assemblies of both FIG. 4 and FIG. 5. The number and order of close adjacency of the sterile fluid basins is selectable in accordance with the preferences of the surgeon and/or the demands of the particular procedure and includes the option of more than one basin containing media maintained at the same thermal state.

Figure 6:
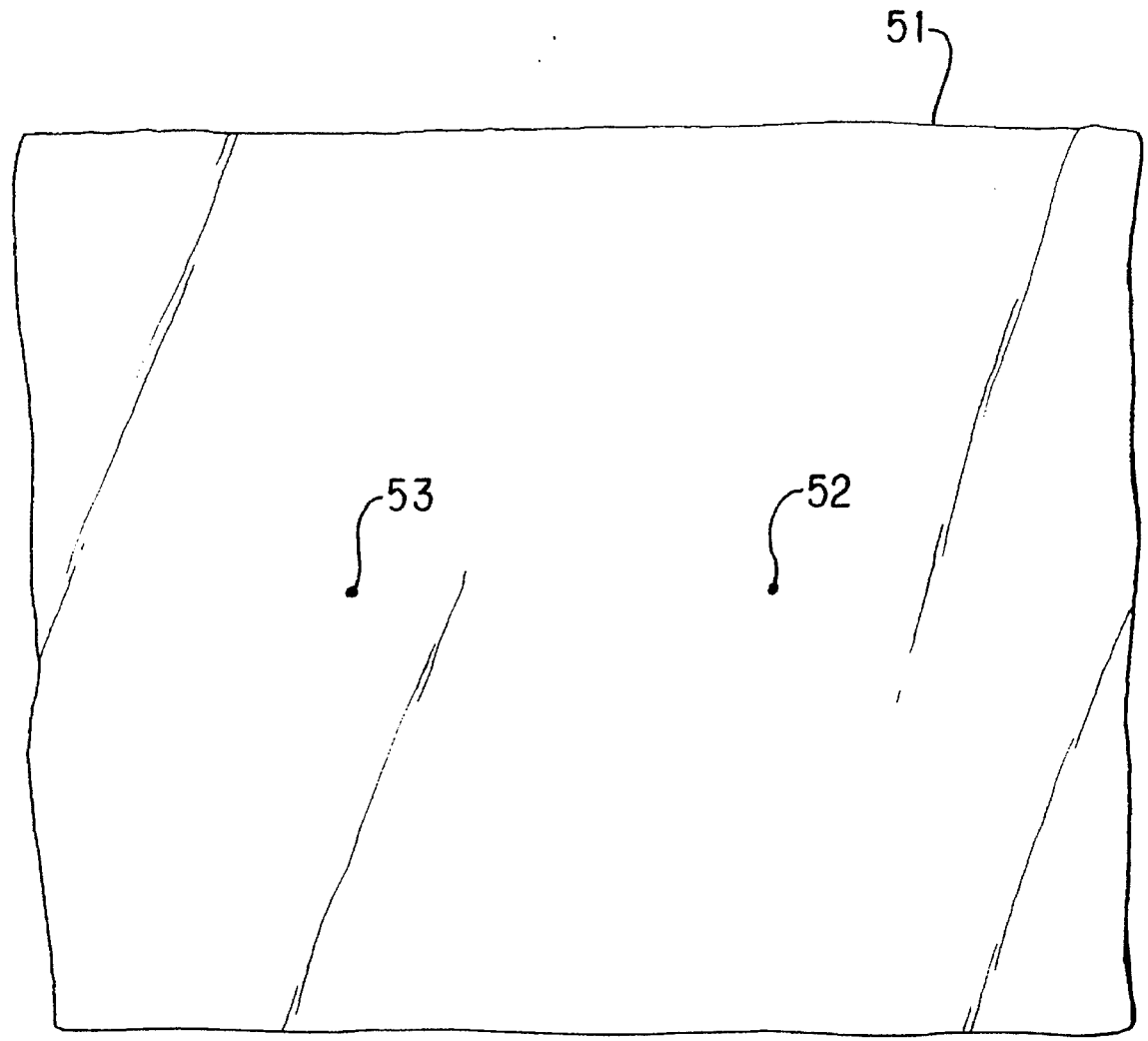
FIG. 6 is a plan view of a surgical drape suitable for use with the embodiments illustrated in FIGS. 1, 2 and 3.

A sterile drape 51, suitable for covering the top surfaces of the combinations of surgical slush units, heater units and chilled liquid units described above (i.e., in FIGS. 1–5), is illustrated in FIG. 6. The drape is made of a material that is impervious to the liquid and slush, and is sufficiently soft and flexible to conform to the basin walls. The thickness of the drape is preferably minimized to render thermal transfer therethrough most efficient, yet sufficiently thick to resist tearing and puncturing of the drape during whisking of slush and other normal use. Typically, by way of example only, the drape is made of materials commonly used in hospitals for surgical drapes and has a thickness in the range of 4.5 to 6.0 mils. The drape 51 may also be made of polyurethane film as disclosed for the drape in the aforementioned Templeton patent. Such drapes are sufficiently transparent to permit power controls and controller/indicators to be observed and operated therethrough. Drape 51 is designed to be disposable after a single use and is provided pre-sterilized and pre-packaged in a leak-proof plastic bag or other sealed container to preserve the sterile nature of the drape during storage.

Figure 7:
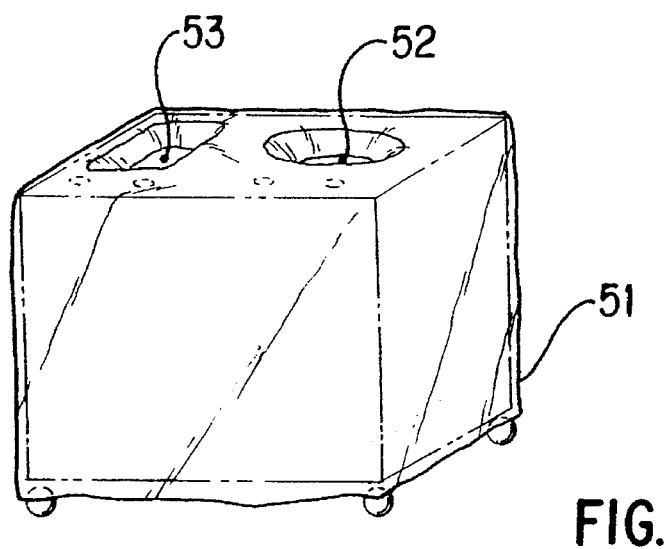
FIG. 7 is a view in perspective showing the surgical drape of FIG. 4 positioned over the unit illustrated in FIG. 3.

An advantageous feature of drape 51 is the provision of centering marks or indicia 52, 53, as shown in FIG. 6 for a two basin application, adapted to be placed over the centers of the basins during installation of the drape. Specifically, the centering indicia are thusly positioned when the drape is pushed down into the basins until it conforms to the basin shapes and forms drape receptacles 54 for the sterile medium. Alternatively, basin-like recesses or receptacles may be formed in the drape and configured to fit directly into the basins. The installed drape, used in conjunction with the embodiment of FIG. 3, is illustrated in FIG. 7. Similarly drapes provided with three or more centering marks appropriately positioned are used for any number and combination of basin units.

Figure 8:
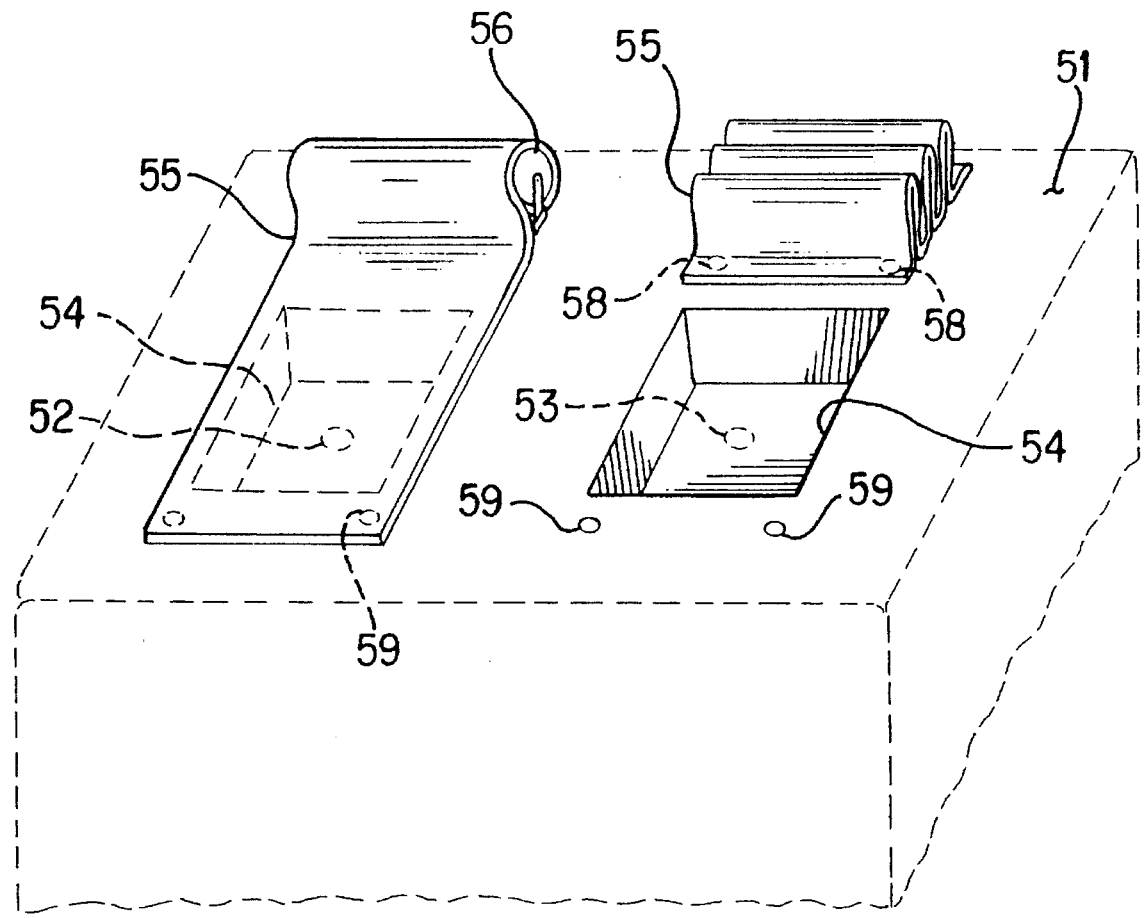
FIG. 8 is a partial view in perspective of a surgical drape with receptacle covers positioned over the unit illustrated in FIG. 3.

As an added enhancement for use with drape 51, flap-like covers 55 may be removably extended to cover medium-containing receptacles 54. A roller 56 is shown in FIG. 8 affixed near one of two drape receptacles. A sheet of drape-like material 57, attached at one end to the roller is selectively unrolled and rolled to cover and uncover the corresponding drape receptacle to provide thermal insulation for the contained sterile medium between periods of required accessibility, and to expose the medium as needed. Also illustrated in FIG. 8, a cover 55 can be a foldaway flap or slidable sheet of material extendable over the receptacle from one side and can be provided with hold-down attachments 58 to interact with corresponding fixtures on the drape 59 to position and secure the cover in place. Alternatively, a peel off adhesive strip affixed to the drape near the edge of the drape receptacle opposite the flap attachment can be used to removably secure the flap across the receptacle.

In addition to providing thermal insulation, cover 55 acts to reduce the unnecessary exposure of the sterile medium to airborne pathogens and, in this regard, can be electrostatically charged to more effectively attract and capture such pathogens.

Figure 9:
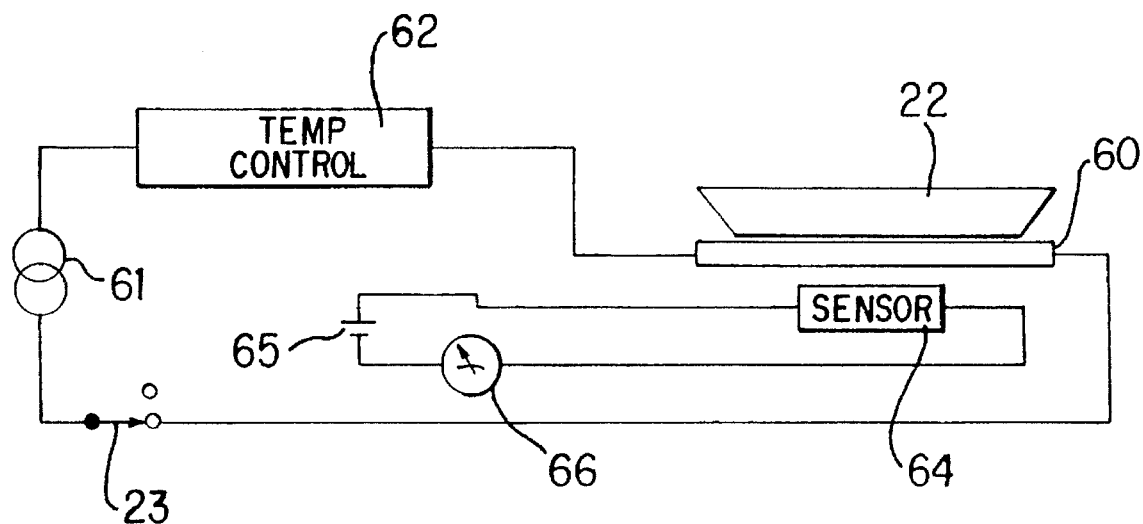
FIG. 9 is an electrical schematic diagram of the heating unit employed in the present invention.

The manner of heating sterile liquid in a heating basin (e.g., heating basin 22 of FIG. 3) is illustrated schematically in FIG. 9. Specifically, an electrical circuit includes a power source 61 connected in series with a temperature control unit 62, a heater element 60 and power control switch 23. Heater 60 is typically a thin wafer-like member disposed along the bottom surface of heating basin 22, secured to the basin by a suitable pressure sensitive adhesive having efficient heat transfer characteristics. Heater 60, may, for example, be of the type described in the aforementioned Templeton patent. Temperature control unit 62 includes a device for adjusting the current passing through the heating element 60 so as to permit selective adjustment of the heat applied to the liquid in basin 22. The power switch 23 permits selective application and removal of current flow with respect to the heater 60.

A temperature sensor 64 is disposed adjacent basin 22 to sense the temperature of the liquid therein. Sensor 64 is connected in series with a voltage source 65 and an indicator 66. Voltage source 65 and power source 61 may be the same source, or the voltage for one may be derived from the other. Indicator 66 measures the current through temperature sensor 64, that current being proportional to the sensed temperature. Indicator 66 and temperature controller 62 may correspond, for example, to the temperature controller/indicators 24 described above.

Figure 10:
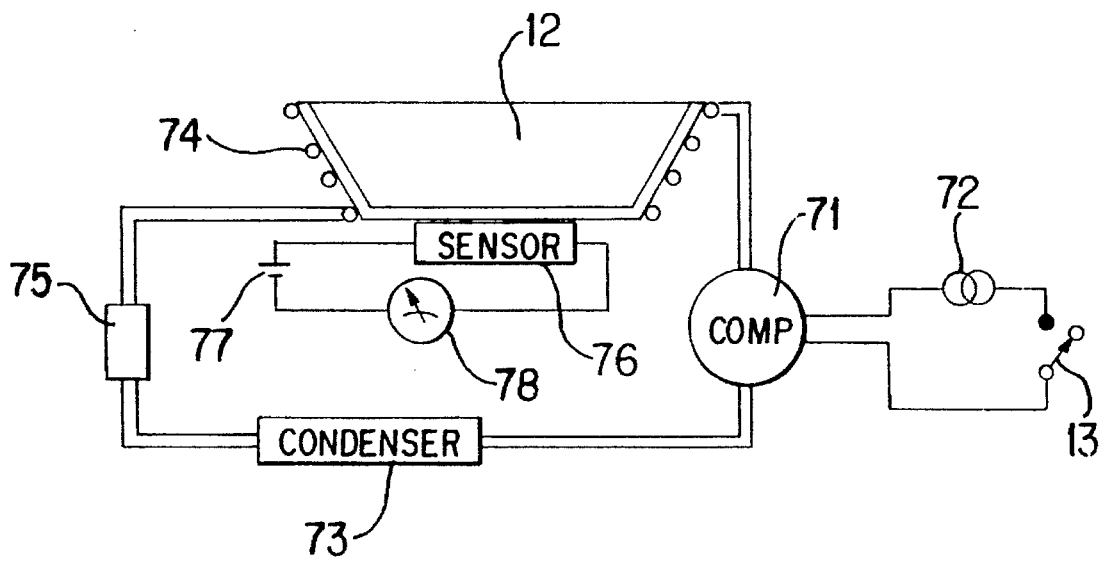
FIG. 10 is a schematic diagram of the cooling system employed in the present invention.

The refrigeration components used to produce and maintain both slush and near-freezing chilled liquid are illustrated schematically in FIG. 10 and include a compressor 71 selectively actuable by means of an electrical power source 72 and an on-off power switch 13. Power source 72 may be the same source as power source 61, but separate power switches are provided for heating and cooling. The compressor 71 causes a suitable refrigerant fluid to flow through a series circuit including a condenser 73, an evaporator 74 and a suitable thermal expansion valve 75. The evaporator 74 is disposed about the sides of slush basin 12 to permit cooling of the basin to a desired temperature. A temperature sensor 76 is disposed along the outside surface of the bottom of basin 12 to monitor the temperature of the chilled liquid or slush formed therein. Sensor 76 is connected in series with a voltage source 77, preferably derived from power source 72, and indicator 78. Indicator 78 measures the current passing through sensor 76 which, in turn, is proportional to the temperature sensed in basin 12.

From the foregoing description it will be appreciated that the invention makes available a novel method and apparatus for permitting combinations of surgical slush and chilled and warmed sterile liquid to be made simultaneously and adjacently available at a surgical procedure.

Having described preferred embodiments of a new and improved method and apparatus for producing surgical slush and chilled and heated sterile liquid in accordance with the present invention, it is believed that other modifications, variations and changes will be suggested to persons skilled in the art after having access to the teachings set forth herein. It is therefore to be understood that all such variations, modifications and changes are believed to fall within the scope of the present invention as defined by the appended claims.

What is claimed is:

1. For employment in a surgical operating room, the method of making available to a surgeon a quantity of a sterile medium, said method comprising the steps of:

(a) covering at least two closely adjacent basins with a sterile drape and contouring said drape to said basins to form drape receptacles within each of said basins;

(b) placing respective quantities of sterile media in said drape receptacles; and (c) transferring thermal energy separately to each of said basins to control the temperature of the medium in each of said drape receptacles.

2. The method of claim 1 wherein the sterile medium in at least one of said drape receptacles is maintained at a temperature to form surgical slush.

3. The method of claim 2 wherein the sterile medium in at least one of said drape receptacles is maintained at a near-freezing chilled liquid temperature.

4. The method of claim 3 wherein the sterile medium in at least one of said drape receptacles is maintained at a temperature above room temperature.

5. The method of claim 2 wherein the sterile medium in at least one of said drape receptacles is maintained at a temperature above room temperature.

6. The method of claim 1 wherein the sterile medium in at least one of said drape receptacles is maintained at a near freezing chilled liquid temperature.

7. The method of claim 6 wherein the sterile medium in at least one of said drape receptacles is maintained at a temperature above room temperature.

8. The method of claim 1 wherein the sterile medium in at least one of said drape receptacles is maintained at a temperature above room temperature.

9. The method of claim 1 further comprising the steps of:

(d) extending said sterile drape over the entirety of a generally horizontal surface in which said basins are recessed; and (e) manually adjusting at least one temperature controller disposed on said surface beneath said sterile drape by manipulating said controls by hand with said drape disposed between said at least one controller and the hand of the operator, thereby to permit manual control of thermal energy transfer in step (c).

10. The method of claim 9 wherein said at least one controller is a power switch and wherein step (e) comprises selectively manually actuating and de-actuating said power switch to, respectively, enable and disable transfer of thermal energy in step (c) to vary the temperature of said sterile medium in said corresponding at least one drape receptacle.

11. The method of claim 9 wherein said at least one controller is a temperature adjustment controller, and wherein step (e) comprises manually adjusting said controller to vary the temperature of said sterile medium in said corresponding at least one drape receptacle.

12. The method of claim 1 further including the step of:
disposing at least two centering indicia on said sterile drape at locations corresponding to the centers of said drape receptacles to facilitate proper positioning of said drape relative to said at least one basin during step (a).

13. The method of claim 1 further comprising the step of protecting and insulating the sterile medium in at least one of said receptacles by selectively attaching a cover over said at least one receptacle between periods of use.

14. For employment in a surgical operating room, the method of making available to a surgeon a quantity of sterile medium, said method comprising the steps of:
(a) covering at least two closely adjacent basins with a sterile drape and contouring said drape to said basins to form drape receptacles within each of said basins;
(b) extending said sterile drape over the top surface and sides of an assembly on which said at least two basins are secured;
(c) placing a quantity of sterile medium in said drape receptacles;
(d) transferring thermal energy from within said assembly to each of said at least two basins to control the temperature of the medium in said drape receptacles; and
(e) disposing at least two centering indicia on said sterile drape at locations corresponding to the centers of said drape receptacles to facilitate proper positioning of said drape relative to said at least two basins during step (a).

15. The method of claim 14 further comprising the step of protecting and insulating the sterile medium in at least one of said receptacles by selectively attaching a cover over said at least one receptacle between periods of use.

16. Apparatus for providing a sterile surgical medium for use by a surgeon in a surgical operating room, said apparatus comprising:
a housing having a top surface and sides;
at least two basins supported in close mutual adjacency on said top surface of said housing;
a sterile drape disposed on said housing covering said top surface and extending along said sides, said drape being conformable to said at least two basins to form drape receptacles in each of said corresponding basins for receiving said sterile surgical medium, said drape being impervious to the sterile surgical medium; and
thermal energy transfer means disposed in said housing for individually and separately controlling the temperature of each of said basins and the sterile surgical medium disposed in said corresponding drape receptacles.

17. The apparatus of claim 16 wherein the sterile medium in at least one of said drape receptacles is maintained at a temperature to form surgical slush.

18. The apparatus of claim 17 wherein the sterile medium in at least one of said drape receptacles is maintained at a near-freezing chilled liquid temperature.

19. The apparatus of claim 18 wherein the sterile medium in at least one of said drape receptacles is maintained at a temperature above room temperature.

20. The apparatus of claim 17 wherein the sterile medium in at least one of said drape receptacles is maintained at a temperature above room temperature.

21. The apparatus of claim 16 wherein the sterile medium in at least one of said drape receptacles is maintained at a near freezing chilled liquid temperature.

22. The apparatus of claim 21 wherein the sterile medium in at least one of said drape receptacles is maintained at a temperature above room temperature.

23. The apparatus of claim 16 wherein the sterile medium in at least one of said drape receptacles is maintained at a temperature above room temperature.

24. The apparatus of claim 16 further comprising at least one manually adjustable controller disposed on said top surface of said housing for controlling operation of said thermal energy transfer means, said controller being manually manipulable by operator's hand with said drape disposed between said controller and the operator's hand.

25. The apparatus of claim 24 wherein said at least one controller is a power switch for selectively actuating and deactuating said thermal transfer means to vary the temperature of said sterile medium in said corresponding at least one drape receptacle.

26. The apparatus of claim 24 wherein said at least one controller is a temperature adjustment controller for selectively varying the temperature of said corresponding at least one basin and the sterile medium in said corresponding at least one drape receptacle.

27. The apparatus of claim 16 wherein said sterile drape includes at least two centering indicia at locations corresponding to the centers of said drape receptacles to facilitate proper placement of said drape relative to said at least two basins.

28. The apparatus of claim 16 wherein said sterile drape includes at least one selectively removable cover extendable over at least one of said drape receptacles.

29. The apparatus of claim 16 comprising a first and a second basin in close mutual adjacency and a single sterile drape extending over said first and second basins forming first and second drape receptacles in said first and second basins for receiving sterile surgical medium.

30. The apparatus of claim 29 wherein said sterile medium in said first and second drape receptacles is maintained at a temperature above room temperature.

31. The apparatus of claim 29 wherein said sterile medium in said first drape receptacle is maintained at a near-freezing chilled liquid temperature and said sterile medium in said second drape receptacle is maintained at a temperature above room temperature.

32. The apparatus of claim 29 wherein said sterile medium in said first drape receptacle is maintained at a near-freezing chilled liquid temperature and said sterile medium in said second drape is maintained at a temperature to form surgical slush.

33. The apparatus of claim 29 wherein said sterile medium in said first and second drape receptacles is maintained at a near-freezing chilled liquid temperature.

34. The apparatus of claim 29 wherein said sterile medium in said first drape receptacle is maintained at a temperature to form surgical slush and said sterile medium in said second drape receptacle is maintained at a temperature above room temperature.

35. The apparatus of claim 16 comprising a first basin, a second basin and a third basin in successive adjacency and a single sterile drape extending over each of said basins forming first, second and third drape receptacles, respectively, in said respective basins for receiving sterile surgical medium.

36. The apparatus of claim 35 wherein said sterile medium in said first drape receptacle is maintained at a temperature above room temperature and said sterile medium in said second and third drape receptacles is maintained at a near-freezing chilled liquid temperature.

37. The apparatus of claim 35 wherein said sterile medium in said first drape receptacle is maintained at a near-freezing chilled liquid temperature and said sterile medium in said second and third receptacles is maintained at a temperature above room temperature.

38. The apparatus of claim 35 wherein said sterile medium in said first drape receptacle is maintained at a temperature above room temperature, said sterile medium in said second drape receptacle is maintained at a near-freezing chilled liquid temperature and said sterile medium in said third drape receptacle is maintained at a temperature to form surgical slush.

39. The apparatus of claim 35 wherein said sterile medium in said first drape is maintained at a temperature to form surgical slush and said sterile medium in said second and third drape receptacles is maintained at a near-freezing chilled liquid temperature.

40. The apparatus of claim 35 wherein said sterile medium in said first drape is maintained at a temperature to form surgical slush and said sterile medium in said second and third drape receptacles is maintained at a temperature above room temperature.

41. The apparatus of claim 35 wherein said sterile medium in said first, second and third drape receptacles is maintained at a temperature above room temperature.

42. The apparatus of claim 35 wherein said sterile medium in said first, second and third drape receptacles is maintained at a near-freezing chilled liquid temperature.

43. Apparatus for providing a sterile surgical medium for use by a surgeon in a surgical operating room, said apparatus comprising:

a housing having a top surface and sides;

at least two basins supported in close adjacency on said top surface of said housing;

a sterile drape disposed on said housing covering said top surface and extending along said sides, said drape being conformable to said at least two basins to form drape receptacles in each of said basins to receive said sterile surgical medium, said drape being impervious to the sterile surgical medium, wherein said drape includes at least two centering indicia at locations corresponding to the centers of said drape receptacles to facilitate proper placement of said drape relative to said at least two basins; and thermal energy transfer means disposed in said housing for controlling the temperature of each of said basins and the sterile surgical medium disposed in said corresponding drape receptacles.

44. The apparatus of claim 43 further comprising at least one selectively removable cover extendable over said at least one of said receptacles for insulating the sterile medium.

* * * * *